(12) United States Patent
Stoller et al.

(10) Patent No.: US 7,776,032 B2
(45) Date of Patent: Aug. 17, 2010

(54) DEVICE FOR IMPROVED VISUALIZATION OF OPERATIVE SITES DURING SURGERY (75) Inventors: Marshall L. Stoller, San Francisco, CA (US); Maxwell V. Meng, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 285 days.

(21) Appl. No.: 11/735,907

(22) Filed: Apr. 16, 2007

(65) Prior Publication Data
US 2007/0191759 A1 Aug. 16, 2007

Related U.S. Application Data (62) Division of application No. 10/222,208, filed on Aug. 16, 2002, now abandoned.

(51) Int. Cl.
A61B 17/00 (2006.01)
A61M 25/00 (2006.01)

(52) U.S. Cl. .............. 606/1; 604/22; 604/23; 604/24; 604/26

(58) Field of Classification Search .......... 606/1; 604/22–24, 26
See application file for complete search history.

(56) References Cited

U.S. PATENT DOCUMENTS

| | | | | |
|---|---|---|---|---|
| 4,941,872 A * | 7/1990 | Felix et al. | .............. | 604/27 |
| 5,085,657 A * | 2/1992 | Ben-Simhon | .............. | 606/42 |
| 5,098,430 A * | 3/1992 | Fleenor | .............. | 606/42 |
| 5,167,220 A * | 12/1992 | Brown | .............. | 600/157 |
| 5,336,170 A * | 8/1994 | Salerno et al. | .............. | 604/24 |
| 5,441,482 A * | 8/1995 | Clague et al. | .............. | 604/35 |
| 5,441,498 A * | 8/1995 | Perkins | .............. | 606/15 |
| 5,449,356 A * | 9/1995 | Walbrink et al. | .............. | 606/49 |
| 5,722,950 A * | 3/1998 | Fujita et al. | .............. | 604/48 |
| 6,296,639 B1 * | 10/2001 | Truckai et al. | .............. | 606/41 |
| 6,375,635 B1 * | 4/2002 | Moutafis et al. | .............. | 604/43 |
| 6,425,877 B1 * | 7/2002 | Edwards | .............. | 604/21 |

* cited by examiner

*Primary Examiner*—Roy D Gibson
*Assistant Examiner*—Kaitlyn E Helling
(74) *Attorney, Agent, or Firm*—Weaver Austin Villeneuve & Sampson LLP (57) ABSTRACT This invention provides a novel surgical device well suited to use in laparoscopic or other (e.g. open surgical) procedures. In certain embodiments, the device comprises a surgical probe, including a handle comprising at least one channel passing through the handle; and at least one conduit passing through the handle, where wherein at least one effector element is inserted into or through the channel, which effector element effects one or more surgical functions; and where the conduit comprises a distal conduit port that directs gas out of the conduit to substantially remove debris and/or fluid from a surface disposed proximal to the effector and/or from the effector element.

3 Claims, 10 Drawing Sheets

DEVICE FOR IMPROVED VISUALIZATION OF OPERATIVE SITES DURING SURGERY

CROSS-REFERENCE TO RELATED APPLICATIONS

This application is a Divisional of U.S. Ser. No. 10/222,208, filed on Aug. 16, 2002, which is incorporated herein by reference in its entirety for all purposes.

STATEMENT AS TO RIGHTS TO INVENTIONS MADE UNDER FEDERALLY SPONSORED RESEARCH AND DEVELOPMENT

[Not Applicable]

FIELD OF THE INVENTION

This invention pertains to the field of medical devices. In particular, this invention provides a surgical probe suitable for laparoscopic, and other surgical procedures, that provides improved surgical site clearance and visualization.

BACKGROUND OF THE INVENTION

One of the most rapidly progressing areas in surgical treatment of patients is minimally invasive surgery, exemplified by laparoscopic surgery. Laparoscopic surgery, which is typically used for surgical treatment within the abdominal cavity, involves conducting the surgical procedure by use of one or more probes inserted through the abdominal wall. The probe (s) delivers the surgical capability into the abdominal cavity. Since only small incision(s) need to be made in the abdominal wall to insert the probe(s) and gain access to the interior organs and tissues, the procedure is regarded as minimally invasive.

To gain access to the abdominal cavity, the abdominal wall is typically penetrated with a device called a trocar. The trocar is attached to a cannula or sheath. After penetration the trocar is withdrawn through the cannula. The abdominal cavity is then pressurized by a flow of gas delivered from an inflation pump through the cannula, and the abdominal wall expands away from the internal organs and tissues. The expansion of the abdominal wall occurs slowly and carefully so as not to damage any of the interior organs or tissues. A pressure sensor on the inflation pump senses the back pressure from the abdominal cavity and terminates the delivery of gas once the pressure reaches an upper limit. The expansion of the abdominal wall provides good access to the interior organs.

After inflation, the probes and other surgical instruments are inserted into the abdominal cavity through a hollow interior of the cannula. A seal on the interior of the cannula contacts the probe to prevent the escape of gas from the abdominal cavity. The probes can then be manipulated from side to side due to the flexibility of the abdominal wall where the cannula penetrates it.

In typical surgeries, a combined light source and video camera device is inserted through one of the cannulas. The interior of the abdominal cavity is illuminated and the images received by the video camera are displayed on a video monitor which is visible to the surgeon. As a result of viewing the video monitor the surgeon is able to manipulate the probes to accomplish the desired surgical effect.

A variety of previous probes are available for use in minimally invasive surgery. However, most of these prior probes are capable of only a single use or type of functionality, for example, standard electrosurgical cutting or coagulation. A few prior art probes may be capable of limited multiple functions, such as standard electrosurgical cutting and coagulation as well as mechanical cutting or biopsy collection.

Typically, however, previous probes simply provide a surgical effector function, e.g. cutting, coagulation, biopsy, etc., and do not facilitate the clearing of the surgical effector and/or the surgical site from fluids or debris.

Many methods of controlling intraoperative bleeding are available, including monopolar electrocautery, bipolar electrocautery, ultrasonic coagulation, and electrothermal bipolar vessel sealing. While reasonable in their efficacy, each has limitations and disadvantages. More importantly, the area must be visualized prior to use of the device using either irrigation and suction or a gauze sponge.

SUMMARY OF THE INVENTION

This invention provides a novel surgical device (probe) that provides a gas jet in addition to one or more surgical effectors. The gas get can be controlled by the operator (e.g., surgeon) to remove debris and fluid from the surface of the surgical effector (e.g. biopsy needle, scalpel, etc.) and/or from the surgical site itself. The gas jet clears the effector and/or the surgical site prior to, during, or after the use of the effector. By clearing blood or other debris, it allows more precise electrocautery, biopsy control, or other effector control.

The gas jet thus serves to improve surgical site clearance and visibility. Moreover, because the action of the gas jet is independent of the activity of the "surgical effector" (surgical instrument), the site and effector surface can be cleared/cleaned prior or during the surgical act.

In one embodiment this invention thus provides a surgical probe, comprising: a handle; at least one channel passing through the handle; and at least one conduit passing through the handle; where at least one effector element is inserted into or through the channel, which effector element effects one or more surgical functions; and where the conduit comprises a distal conduit port (e.g. nozzle) that directs gas out of the conduit to substantially remove debris and/or fluid from a surface disposed proximal to the effector element and/or from the effector element itself. In certain embodiments, the effector element is removable from the probe, while in other embodiments, the effector element (e.g. surgical effector) is "permanently" affixed to the probe. The probe handle can further comprise a control to regulate gas flow through the conduit and/or a to regulate activity of the effector element. The distal conduit port can comprise a nozzle to regulate gas jet shape and/or force. The nozzle can be one of a number of interchangeable nozzles to provide different gas jet forces and/or patterns, or the nozzle can be adjustable to provide different gas jet forces and/or patterns In certain embodiments, the conduit and tie channel are disposed within a tube within the probe handle. In certain embodiments, the handle can be removable from the tube. Certain preferred probes are suitable for a laparoscopic procedure. Certain preferred probes are suitable for an open surgical procedure.

In some embodiments the effector element comprises at least one scalpel or cautery and/or at least one or more forceps, and/or at least one syringe. Certain probes comprise an effector for performing at least one laparoscopic surgical function. In certain embodiments, the effector element (e.g. surgical effector) performs a function such as visualizing tissue, anesthetizing tissue, incising tissue, cauterizing tissue, dissecting tissue, grasping, desiccating tissue, irrigating tissue, resecting tissue, delivering at least one therapeutic agent to tissue, aspirating fluids from tissue, biopsying tissue, and/ or suturing tissue. One preferred effector comprises a cauterization device (e.g. a monopolar cauterization device, a biopolar cauterization device, etc.). In certain embodiments, the effector element comprises at least one optical lens (e.g. a lens operably connected to at least one monitor to display images formed by the optical lens). In certain embodiments, the effector element can comprise at least one fluid channel (e.g. a fluid channel operably connected to a fluid source). The fluid channel can be disposed so that fluid flows out of the fluid channel from the fluid source to irrigate tissue disposed proximal to the probe. In certain embodiments the effector element can comprise at least one electrode element (e.g. an electrode element operably connected to an electrical energy source). Typically, the electrical energy can be conducted through the electrode element from an electrical energy source to a surface where the electrical energy incises and/or cauterizes tissue disposed proximal to said surface. In certain embodiments, the effector element comprises at least one fiber optic cable (e.g. a fiber optic cable is operably connected to a laser source). In some embodiments, radiation is conveyed through fiber optic cable from said laser source to the probe surface whereby the radiation incises and/or cauterizes tissue disposed proximal to the surface.

In certain embodiments, the probe is removably insertable into and through a cannula. Certain preferred probes comprise a length between about one cm and about 50 cm. The probe can be substantially rigid or flexible. The probe can comprise a handle comprising at least one non-combustible gas source operably connected to the conduit. The gas source can be in the handle or external to the handle. The handle can further comprise a control for controlling the gas flow and/or a control for controlling the effector. In certain embodiments, both controls are integrated into a single control. Thus, in certain embodiments, the handle comprises at least one control operably connected to the conduit and/or operably connectable to the effector element. In various embodiments, the gas and/or electrical energy controls can be manually operated (hand operated, foot operated), robotically operated, voice actuated, and the like. The control(s) can comprise at least one switch and/or at least one valve.

In certain embodiments, the effector element and the non-combustible gas flow are simultaneously operable. The effector can, optionally, be extendable from a first end of the probe. The portion of the effector can comprise at least one electrode element. In some embodiments, the portion extends between about one mm and about 50 mm from the end of the probe. The effector portion can be linear, non-linear, or malleable and can have virtually any shape (e.g. a regular n-sided polygon, an irregular n-sided polygon, a triangle, a square, a rectangle, a trapezoid, a circle, an oval, etc.).

In another embodiment, this invention provides a method of performing a surgical procedure. The method involves providing a surgical probe as described herein; and operating the probe to produce a flow of a non-combustible gas (e.g. carbon dioxide, nitrogen, helium, etc.) through the conduit to remove blood or debris from the tip of a surgical effector comprising the probe and/or from a tissue surface, while said probe is inserted into the body cavity of a mammal (e.g. a surgical patient). In certain embodiments the effector is a cauterization device (e.g. a monopolar cauterization device, a bipolar cauterization device, etc.). The cauterization device can be used to reduce bleeding and/or to cut a tissue (e.g. any internal organ such as kidney, liver, spleen, heart, gall bladder, stomach, intestine, etc.). The gas jet can also be used to deliver an agent (e.g. a pharmaceutically active agent). Preferred agents include, but are not limited to various pharmaceuticals, biologically compatible microbicides, antibiotics, antivirals, and the like).

In certain embodiments, the probe is used to irrigate and/or to mist a surgical site with a fluid (e.g. saline, a dissolved pharmaceutical, etc). The debris removed can include cellular and/or acellular material(s) or fluid(s). In certain embodiments, the debris comprises one or more materials selected from the group consisting blood, an organ, cartilage, bone, urine, lymphatic fluid, bile, cartilage, and bone. The tissue surface can comprise an internal and/or an external bodily surface and/or a lumenal surface.

In still yet another embodiment, this invention provides a surgical device, comprising: a handle; where at least one channel passes through the handle; and at least one conduit passes through said handle; where said channel can receive and support a surgical effector inserted into or through the channel; and wherein the conduit comprises a distal conduit port that directs gas out of the conduit to substantially remove debris and/or fluid from a surface disposed proximal to a surgical effector tip when said surgical effector is inserted into said channel. The handle can, optionally, comprise a control to regulate gas flow through the conduit and/or a control to operate the surgical effector. The conduit and the channel can be disposed within a tube within the handle and in certain embodiments, the handle is removable from the tube. The device can be suitable for a laparoscopic procedure and/or for an open surgical procedure. In some embodiments, the surgical effector comprises at least at least one scalpel or cautery (e.g. steel scalpel, laser scalpel, electro-scalpel, monopolar cauterization device, bipolar cauterization device, etc.). The device can further comprise at least one non-combustible gas source disposed within the handle. In certain embodiments, the gas and/or the surgical effector can be controlled, e.g. as described above.

In still another embodiment, this invention provides a kit comprising: a container containing a surgical probe as described herein. The kit can further comprise one or more surgical effectors that are insertable into the channel comprising the handle of the probe. Certain kits comprise an effector having surgical function selected from the group consisting of: visualizing tissue, anesthetizing tissue, incising tissue, cauterizing tissue, dissecting tissue, desiccating tissue, irrigating tissue, resecting tissue, delivering at least one therapeutic agent to tissue, aspirating fluids from tissue, biopsying tissue, and suturing tissue. In certain kits, one or more surgical effectors is a cauterization device. The kit can further comprising one or more replaceable tips for the cauterization device. The kit can, optionally, further comprise instructional materials that directs use of the surgical device.

This invention also provides a surgical system comprising a probe comprising at least one electrode and at least one conduit, where the electrode is operably connected to an electrical energy source and at least a portion of the electrode extends from a first end of said probe, and where electrical energy is conducted through said portion from the electrical energy source to tissue disposed proximal to the portion to incise and/or cauterize said tissue, and where the conduit is operably connected to at least one non-combustible gas source and at least one terminus of the conduit is disposed proximal to said first end of said probe component, and where a non-combustible gas is flowed through said conduit from the non-combustible gas source and out of the terminus to substantially remove debris from tissue disposed proximal to said portion and/or from the portion; and a handle connected to the probe, which handle comprises at least one control to control electrical energy conduction from the electrical energy source and/or non-combustible gas flow from said non-combustible gas source. In certain systems, the probe is removably insertable into and through a cannula. In certain embodiments, the probe comprises a length between about one cm and about 50 cm, preferably between about 5 and 45 cm, more preferably between about 10 and 35 cm. In certain embodiments, the probe is substantially rigid, while in other embodiments, the probe is flexible. The electrode element can be integral with the probe or it can be removable. In certain embodiments, at least one edge of portion is non-linear. In certain embodiments, the portion extends between about one mm and about 50 mm from the first end of said probe component. The electrode portion can have any convenient shape (e.g. a regular n-sided polygon, an irregular n-sided polygon, a triangle, a square, a rectangle, a trapezoid, a circle, an oval, etc.). In certain embodiments, the conduit comprises a tube. The terminus of the conduit can comprise at least one nozzle to focus and/or shape the non-combustible gas (e.g. carbon dioxide, helium, nitrogen, etc.) that is flowed out of the terminus. The handle can also comprise the electrical energy source and/or the gas source. In various embodiments, the gas and/or electrical energy controls can be manually operated (hand operated, foot operated), robotically operated, voice actuated, and the like. The control(s) can comprise at least one switch and/or at least one valve.

This invention also provides a method of substantially removing debris from a surface and/or from a surgical device. The method comprises providing said surgical device, which surgical device comprises at least one effector element that effects one or more surgical functions and at least one conduit, which conduit is operably connected to at least one non-combustible gas source; and, flowing a non-combustible gas from the non-combustible gas source out of said conduit to substantially remove said debris from the surface disposed proximal to said effector element and/or from said effector element. The surgical device can be suitable for laparoscopic methods and/or for open surgical procedures. The debris removed can include cellular and/or acellular material(s) or fluid(s). In certain embodiments, the debris comprises one or more materials selected from the group consisting blood, an organ, cartilage, bone, urine, lymphatic fluid, bile, cartilage, and bone. The tissue surface can comprise an internal and/or an external bodily surface and/or a lumenal surface. In certain embodiments, the surgical device comprises at least one cavity into or through which said effector element is removably inserted, while in certain other embodiments, the effector is removable. Preferred effector elements include, but are not limited to an electrode, a laser fiber optic cable, a mechanical device, and the like. In certain embodiments, the device comprises the effector element and the conduit, and the method further comprises inserting at least a segment of the device into and through a cannula disposed through a body wall of a patient prior to flowing the non-combustible gas. In certain embodiments, the method involves insufflating a body cavity of said patient by flowing a quantity of said non-combustible gas out of the conduit prior to the flowing step. The method can then further comprise effecting the surgical functions with said effector element(s). In certain embodiments, the surgical device comprises at least one cavity into or through which the effector element is removably inserted, and where the method further comprises exchanging a different effector element with a first effector element to a effect a different surgical function. The debris can be substantially removed prior to and/or simultaneous with effecting the surgical functions.

In another embodiment, this invention provides a method of performing a surgical procedure where the method involves providing a surgical probe as described herein and operating the probe to produce a flow of a non-combustible gas through the conduit where the gas comprises an aerosolized agent and the flow of gas delivers the agent to a surgical site. In certain embodiments, the agent is a pharmaceutically active agent (e.g. a microbicide, an antibiotic, etc.).

In certain embodiments, the devices and methods of this invention expressly exclude a combustible gas, and/or an argon gas jet, and or a mist and/or a saline or water mist.

Definitions.

The term "surgical effector" refers to a device (e.g. a surgical instrument) that implements a surgical function (e.g. cutting, coagulation, biopsy, cauterization, spreading, grasping, pulling, etc.). Various surgical effectors include, but are not limited to scalpels, forceps, spreaders, tissue lifters, probes, and the like.

The term "surgical effector support equipment" refers to auxiliary equipment that may be required to operate certain surgical effectors. Thus, for example, where the surgical effector is a laser, the surgical effector support equipment may comprise a power source and controls to operate the laser. Where the surgical effector is an electrocauterization device, the surgical effector support equipment may comprise an energy source for the cautery device. Certain surgical effectors may require no surgical effector support equipment.

The term "operably linked", when used with respect to "surgical effector support equipment" refers "connections" between the support equipment and the effector that permits the effector to function in the desired manner. For example, a cauterization device may be operably linked to a power source by a power cable.

A "pharmaceutically active agent" refers to an agent that has a biological activity, more preferably a medically desirable biological activity. Pharmaceutically active agents include pharmaceuticals, biologically compatible disinfectants, antibiotics, antiviral agents, vasoconstrictors, vasodilators, muscle relaxants, and the like.

BRIEF DESCRIPTION OF THE DRAWINGS

FIG. 1 provides a schematic illustration of a surgical probe 20 illustrating the gas conduit 24, and the channel for receiving a surgical effector 22. While this figure illustrates the channel 22 extending the entire length of the probe, in certain embodiments, the channel 22 only extends partially through the probe from the distal end 18.

FIG. 2 schematically illustrates an embodiment of probe 20 incorporating a surgical effector that provides cutting or cauterization.

FIGS. 3A and 3B schematically illustrate embodiments of probe 20 where the gas conduit 24 passes through the instrument channel 22 and/or through the surgical effector 26. In FIG. 3A, the gas source 32 is external to the probe. In FIG. 3B, the gas source is internal to the probe (e.g. a small gas cylinder).

FIG. 4 schematically illustrates an embodiment of probe 20 where channel 22 and/or the surgical effector 26 passes through the conduit 22.

FIG. 5 illustrates one embodiment of probe 20 is shown as it would typically be used in a minimally invasive surgical procedure in an abdominal or body cavity 122.

FIGS. 6A and 6B illustrate various cross-sections of an embodiment of probe 20. FIG. 6A illustrates a cross-section of an embodiment of probe 20 with the surgical effector 26 removed. FIG. 6B illustrates a cross-section of an embodiment of probe 20 with the surgical effector 26 in place.

FIG. 7 illustrates a probe 20 and several effector tips.

DETAILED DESCRIPTION

This invention pertains to novel devices useful in laparoscopic and other surgical procedures (e.g. open surgical procedures). A major difficulty during laparoscopic surgery is insuring meticulous homeostasis and adequate visualization. This invention provides a novel device that provides enhanced visualization using a focused jet of typically non-combustible gas or gasses, and/or mist, that clears the tissue from pooled fluid, debris, and blood. The device can additionally incorporate one or more surgical effectors. The surgical effectors can comprise can include one or more of a number of surgical devices, and in certain embodiments, includes a device that has the ability to cut and coagulate (e.g. via cautery) with electricity, flame, or heat (e.g. laser). The gas jet also allows the tip of the surgical effector to be cleaned of debris or fluids.

Because the gas jet can be controlled independently of the surgical effector, the surgical site can be cleared to provide improved visibility before taking any action that might damage the underlying tissue.

While the devices of this invention are well suited to laparoscopic uses, they are also well suited for a number of other, e.g. open surgical procedures. Thus, for example, the devices of this invention can readily be used to improve site clearance and visualization during electrocautery in an open surgical procedure.

Figure 1:
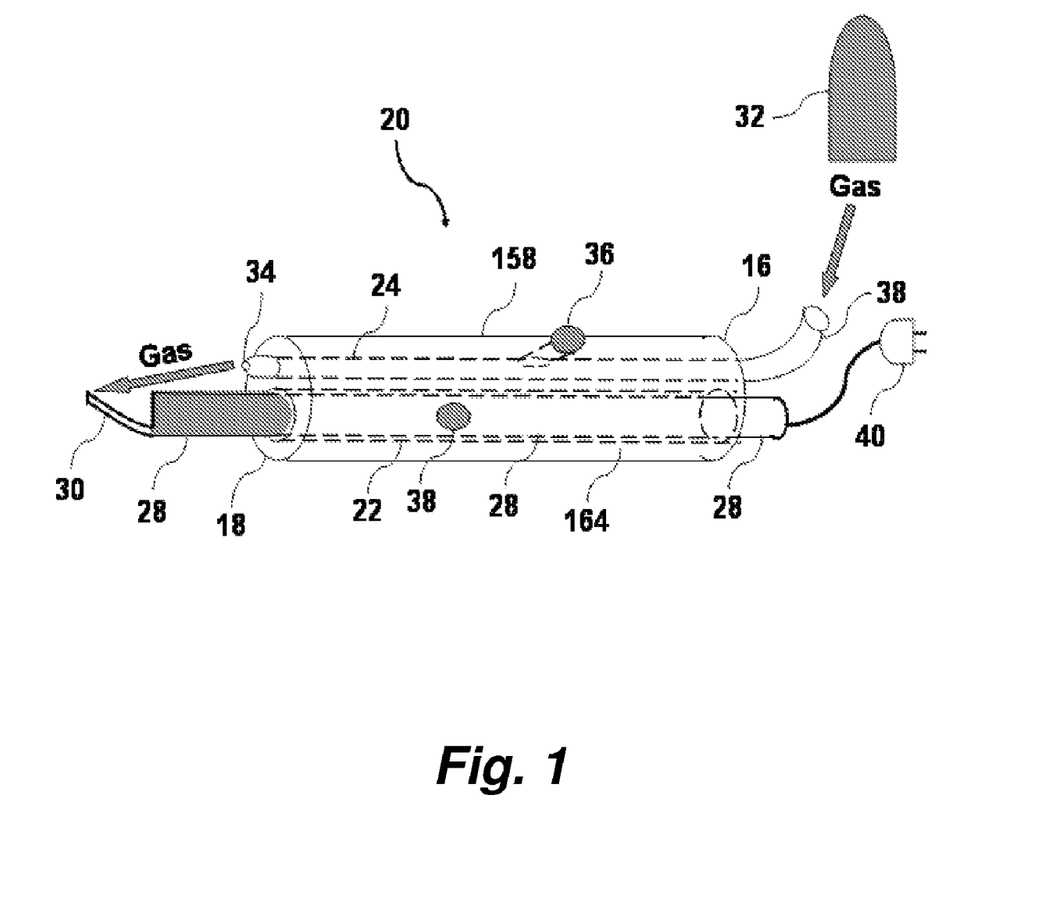

One embodiment of the surgical device is schematically illustrated in FIG. 1. The surgical device comprises a probe 20 comprising a proximal end 16 and a distal end 18. The probe also comprises at least one cavity or channel 22 and at least one conduit 24. The cavity or channel provides for insertion and/or temporary or permanent attachment of at least one surgical effector element 28. In FIG. 1, the device is illustrated wherein the effector is an electrocauterization device 28 that permits cutting or cauterization of a tissue.

Figure 3A:
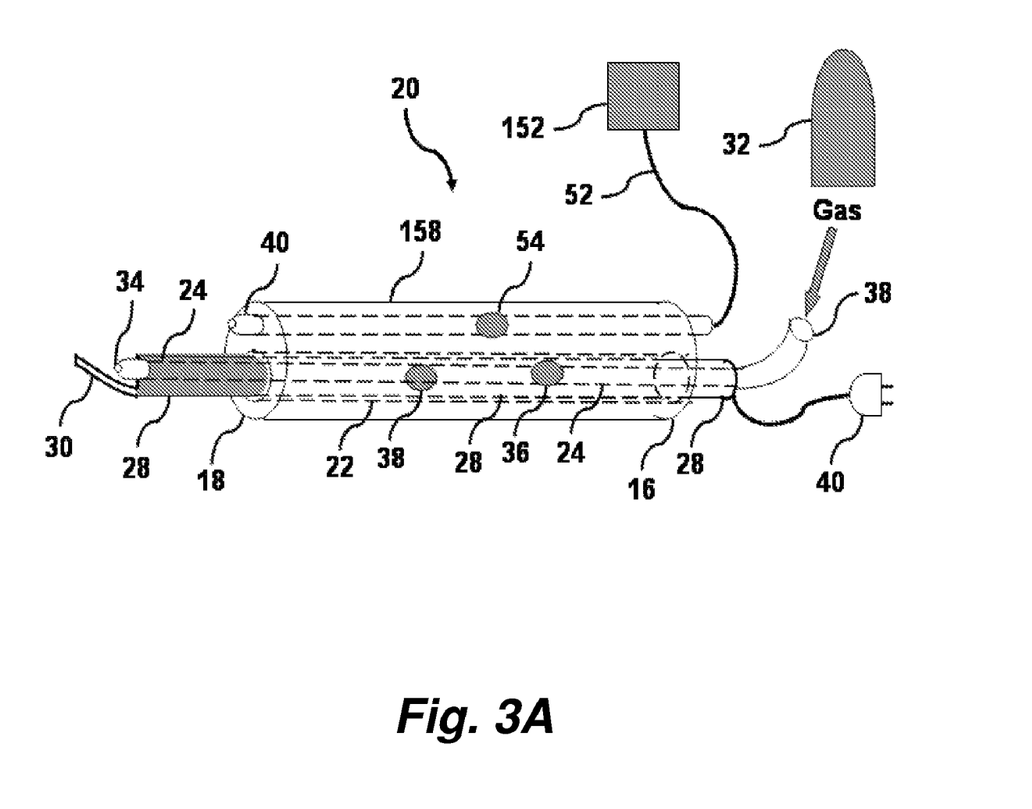
Figure 3B:
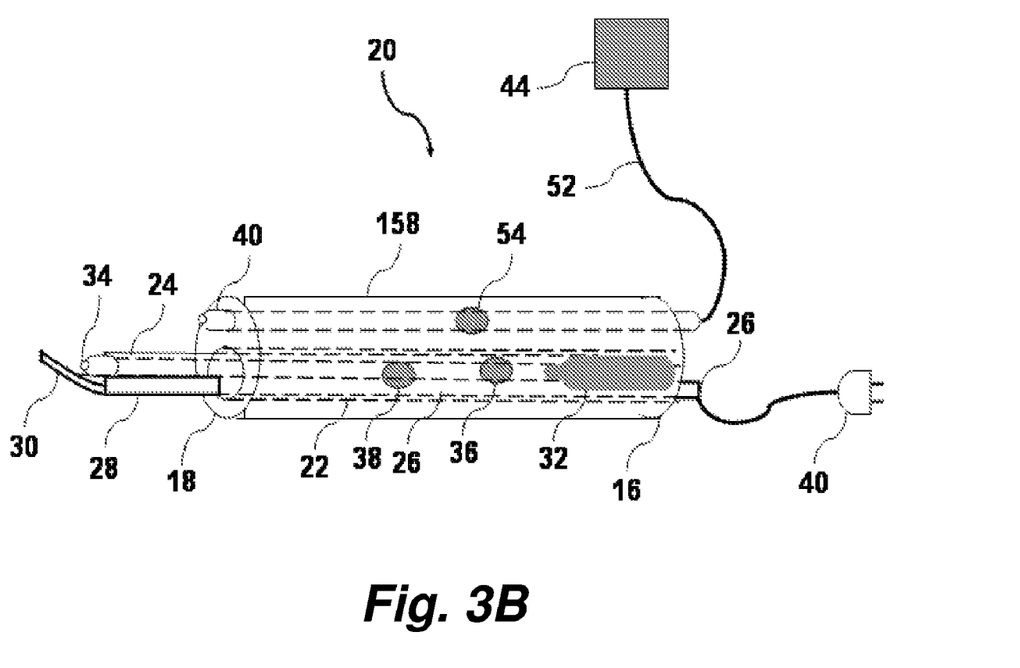

In typical usage, the device is coupled (e.g. via a flexible tube 38) to a source of gas 32, preferably non-combustible gas (e.g., carbon dioxide, nitrogen, helium, etc.) or combination of gasses and/or one or more mists (e.g. saline mist, disinfectant mist, antibiotic mist, etc.). Alternatively, the gas source can be located within handle as illustrated in FIG. 3B. In the illustrated embodiment, the gas is provided by a small canister that fits within the handle. Gas flow is regulated by control 36.

Gas passes through the conduit 24 to exit through the conduit port (nozzle) 34. The gas is directed, e.g. by the conduit port 34 to the tip of the surgical effector 30 and/or to points distal to or adjacent to said tip. The gas jet produced through the conduit port acts to clean the effector tip 30 and/or to blow debris and fluid (e.g. blood, cellular debris, etc.) away from the surgical site thereby improving visibility. In certain embodiments, the probe is provided with a gas flow control 36 that allows the operator to easily regulate the flow of gas through the device.

In various embodiments, the effector element is operably linked to a power/energy source, and/or a gas or vacuum source, and/or a light source, and/or a fluid source to facilitate implementation of the particular surgical effector function. FIG. 1 illustrates the electrocauterization effector operably linked to a power source 40. The probe is also optionally provided with an effector control 38 to regulate the activity of the effector. Thus, in the illustrated embodiment, the control 38 can turn the cauterization device on and set it to cut or to cauterize.

While FIG. 1 illustrates the controls 36 and 38 mounted on the probe 20, such locations are simply illustrative. In various embodiments, this invention contemplates a variety of locations/modes for one or both controls. Thus, in various embodiments, this invention contemplates foot-pedal control, control by another operator, voice activation/control, computer control, robotic control, control by manipulators or micromanipulators, and the like.

Any of a number of methods of regulating gas flow can be used to control the gas flow through the conduit 24. Any of a number of valves (including, but not limited to, pinch valves, gate valves, thumbwheel operated valves, and the like) are suitable. In various embodiments, the probe can simply provide a channel from the conduit 24 to the surface of the probe. Partial or complete obstruction of the channel, e.g. by the finger of the operator, can regulate the gas pressure through the conduit port (nozzle) 34.

The device can comprise a fixed nozzle 34, or, in certain embodiments, can accommodate any of a variety of interchangeable nozzles. By varying the nozzle type, the force, pattern, and dispersion of the gas jet can be varied and/or optimized for a particular surgical site.

Figure 2:
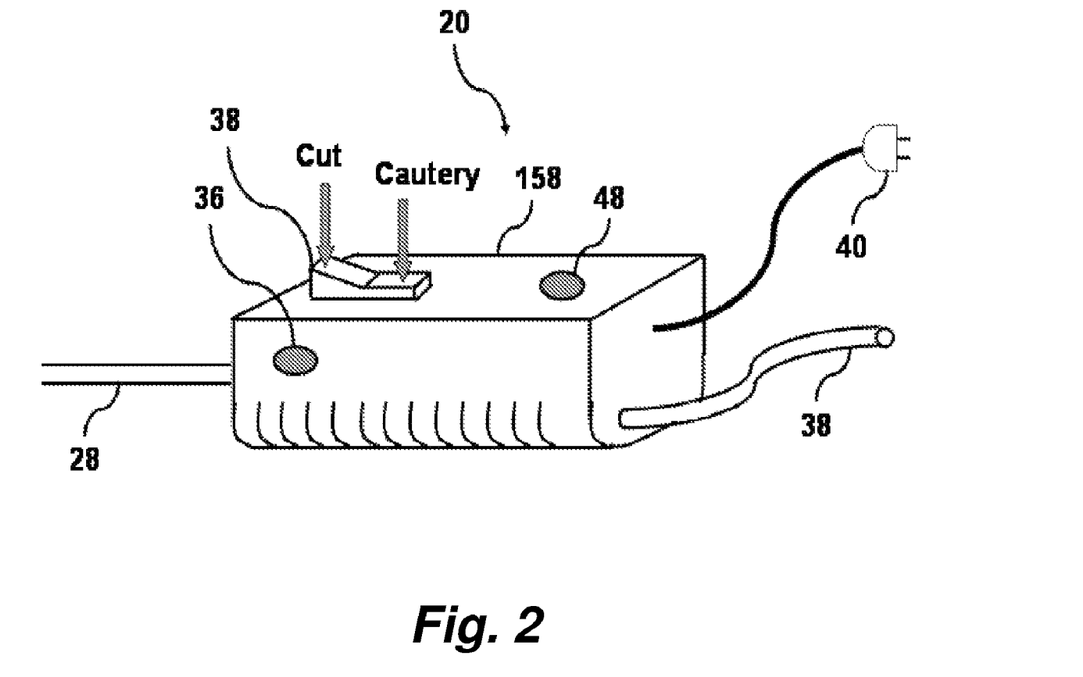

FIG. 2 illustrates another embodiment, of the surgical device of this invention. In this embodiment, the effector control 38 is illustrated as a rocker switch that switches between cutting and cautery. The switch could also be a 3 position rocker switch that switches between cutting, off, and cautery. Alternatively, the on/off status of the device could be determined by another control (e.g. a foot pedal). Gas flow is operated by control 36 as described above. The illustrated device also provides a third functionality (e.g. illumination, vacuum/suction, etc.) operated by control 48. While the tip 28 can be long (e.g. 45 cm) for laparoscopic purposes, the tip can also be shorter, e.g. for open surgery.

While in the embodiment of the surgical device of FIG. 1, the conduit 24 is illustrated as separate from the cavity 22, the invention need not be so limited. FIGS. 3A and 3B illustrate embodiments where the conduit 24 is disposed within the cavity 22. In certain embodiments, the conduit 24 can even be disposed within the one effector element 28 and/or the effector element support 26.

The surgical device need not be limited to a single effector. Embodiments comprising two, three, or even more effectors are also contemplated. The device illustrated in FIG. 3 shows two effectors. The first is an electrocauterization device 28, while the second is a light or illumination source or laser 40. The second effector 40 is shown operably linked to a controller 152 (effector support equipment) by a power/control cable 52. The second effector is conveniently operated using the control 54.

Figure 4:
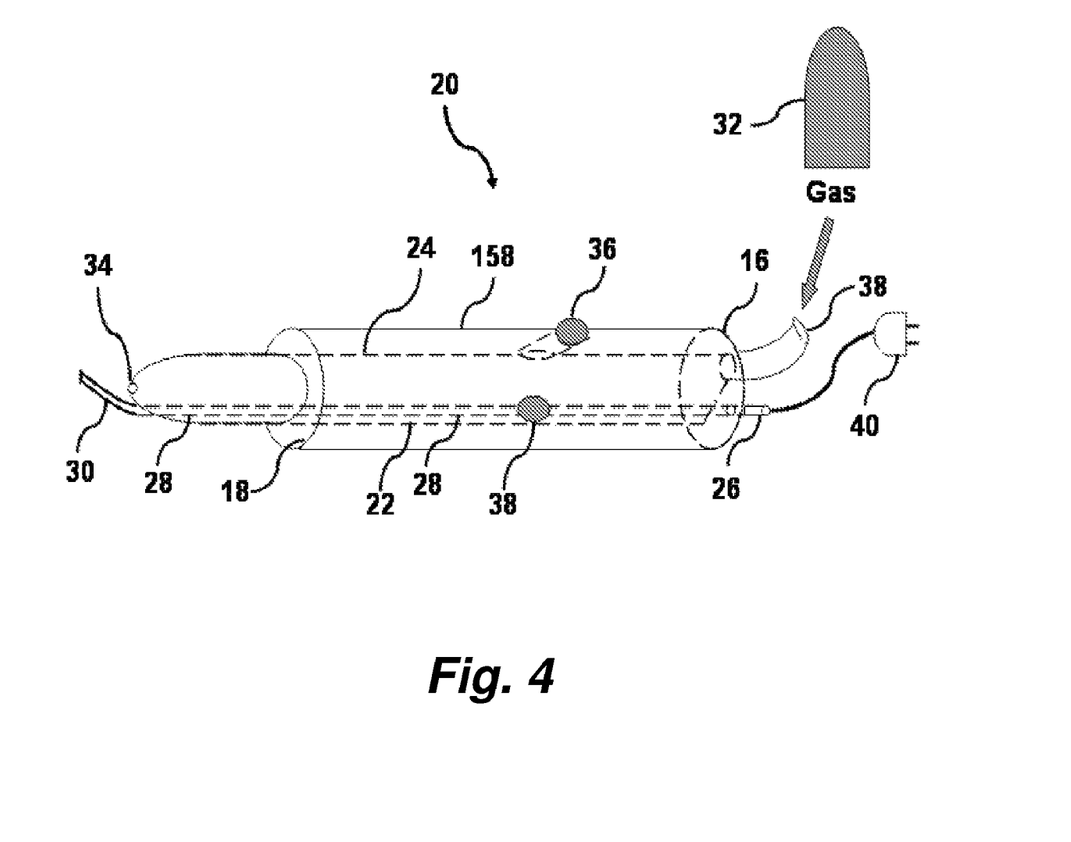

FIG. 4 illustrates an embodiment, where the cavity 22 and/or receptacle for the effector element 28 is disposed within the conduit 24.

Figure 5:
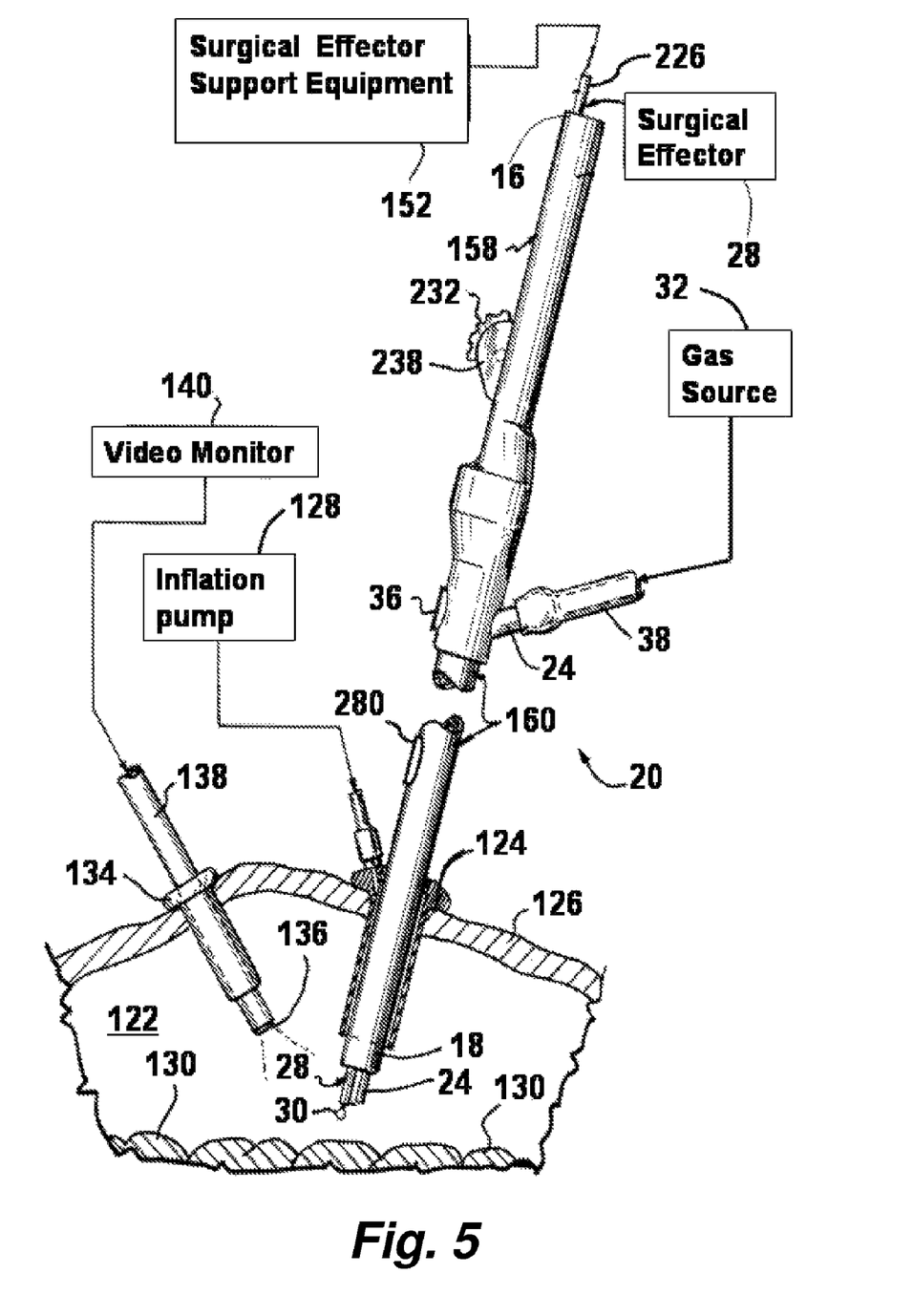

In FIG. 5, the probe 20 is shown as it would typically be used in a minimally invasive surgical procedure in an abdominal or body cavity 122. The probe 20 is inserted into the abdominal cavity through a cannula 124 which has previously been passed through the abdominal body or wall 126. An inflation pump 128 forces pressurized and sterile gas, such as carbon dioxide, through the cannula 124 into the abdominal cavity 122. As a result, the abdominal wall 126 expands away from the interior tissues and abdominal organs 130. A pressure sensor of the inflation pump 128 controls the operation of the pump 128 to limit the amount of pressure within the abdominal cavity 122 and thereby limits the amount of expansion of the abdominal wall 126. A second cannula 134, and possibly others as determined by the surgeon, can also be positioned in the abdominal wall 126, but the additional cannulas are not necessarily attached to the inflation pump 128.

A video camera and light source device 136 can be connected to a wand-like device 138. The wand-like device 138 can be inserted into the abdominal cavity 122 through the cannula 134. The light source of the device 136 illuminates the interior tissues and organs 130, and the video camera of the device 136 transmits video images to a video monitor 140. By viewing the interior organs 130, the surgeon is able to manipulate the probe 20 to achieve a desired surgical effect.

As indicated above, the probe 20 comprises a conduit 24 ultimately connected to a gas source 32. As illustrated in FIG. 3A, a tube 38 conducts gas from the gas source 32 to the conduit 24 which then delivers the gas through the conduit port (nozzle) 34. Gas flow is regulated by the gas flow control 36. Gas emerging from the conduit port blows fluid and particulate matter off of the surgical instrument tip 30 and off of any tissue surfaces nearby, e.g. adjacent to the instrument tip thereby improving visibility. While this embodiment is visualized connected to a separate tank via tubing to provide the gas, in certain embodiments, the gas can be provided by a disposable, self-contained pressurized gas cylinder that fits within the hand piece, e.g. as illustrated in FIG. 3B.

The probe 20 offers the capability of accepting and utilizing a variety surgical effector elements 28, such as a standard electrosurgical cutting and coagulation electrode, a laser fiber optic conduit for cutting and coagulation, an aqua dissection conduit, mechanical tools such as a knife or a biopsy collection device, and other types of surgical equipment. In various embodiments, the surgical effector elements can be inserted into the probe 20 from its rear or proximal end 16, and/or, when the probe is removed from the cannula, from the distal end 18. Depending on the type of surgical effector (surgical instrument) 28 used with the probe 20, the instrument 28 may need to be connected to support equipment 152 by which to use the auxiliary surgical instrument 28. For example, if the instrument 28 is a standard electrosurgical electrode, the support equipment can be a standard electrosurgical generator. When a laser fiber optic conduit is used as the surgical effector instrument with the probe 20, the laser fiber optic conduit can be connected to a laser beam device. When an aqua dissection conduit is used as the auxiliary surgical instrument, the aqua dissection conduit can be connected to a fluid pressure and flow generation device. Of course, if a mechanical tool is used as the auxiliary surgical instrument, it may or may not be connected to support equipment, since manual control of many mechanical tools by the surgeon will operate them without additional support equipment.

As a result of the images on the video monitor 140 obtained from the video camera of the device 136, the surgeon can grasp a handle 158 of the probe 20 and manipulate a connected tube 160 of the probe 20 to position the distal end 18 at the desired location to achieve the desired surgical effect on the tissue or organs 130. The probe can be pivoted along with the cannula 124 at the point where both extend through the abdominal wall to move the distal end 18 to the desired location.

The handle 158 and the tube 160 and the effector element 28 can be permanently connected together as a unitary structure by an adhesive, by welding, or the like. Preferably the handle 158 and the tube 160 and all of the components associated with these elements other than the metallic and elastomeric components are formed of plastic, to obtain a relatively inexpensive and disposable probe 20. Of course, the probe 20 can also be formed of more long lasting and durable materials that are capable of repeated sterilizations, in order to allow the probe 20 to be used repeatedly before disposal.

In addition to the conduit 24, the tube 160 also includes an instrument channel 22 that can extend parallel to the conduit 24 along the length of the tube. The instrument channel 22 can communicate directly with the interior of the handle 164 as is shown in FIG. 1. The channel 22 can extend continuously and longitudinally through the probe 20 from the distal end 18 at the tube 160 to the proximal end 16 at the handle 158. It is through this channel 22 that the various auxiliary surgical instruments (surgical effectors) can be utilized in conjunction with the probe 20, e.g. as described above.

The channel 22, however need note extend the full length of the probe. In certain embodiments, the channel 22 extends from the distal end 18, partway back into the tube 160 and/or the handle 158. In such embodiments, surgical effectors can be inserted and removed from the distal end of the probe 20 or such effectors can be permanently mounted in the probe 20.

In certain embodiments, the surgical effectors (surgical instruments) used with the probe 20 should be generally elongated and have an exterior to fit within the channel 100 (e.g. a cylindrical shape, a rectangular shape, a square shape, a triangular shape, etc.). One such variation is illustrated in FIG. 6.

Figure 6A:
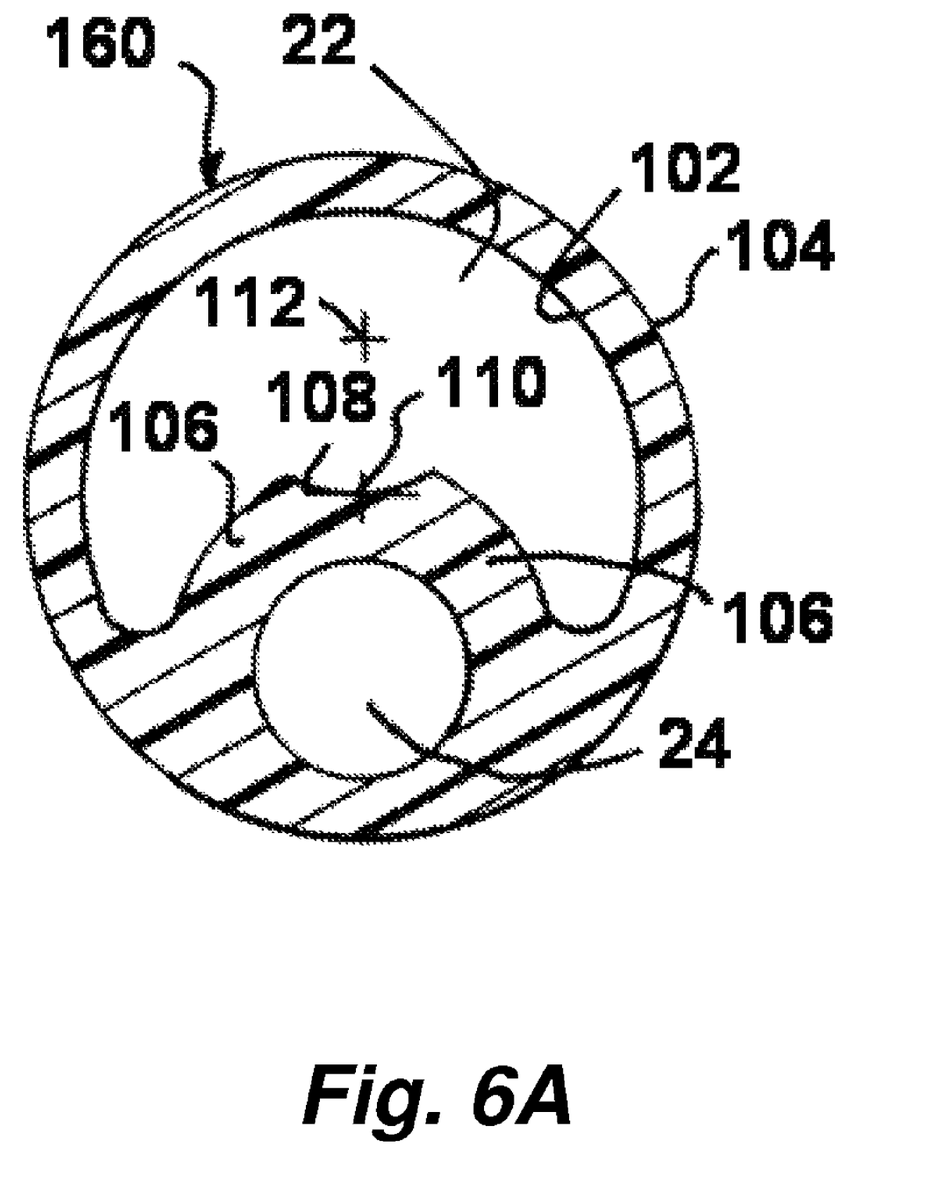

As shown in FIG. 6A, a cross sectional view of the channel 22 reveals a crescent shaped configuration. An inner cylindrical wall 102 of the tube 160 is generally parallel to the outer cylindrical wall 104 of the tube 160. An inner partition 106 within the tube projects radially inward from both points at which the inner cylindrical wall 102 terminates. The partition 106 separates the conduit 24 from the channel 22 along the length of the tube 160. As illustrated, the partition 106 has a cylindrically curved support surface 108 that faces radially outward. The inner most location of concavity of the support surface 108 is at the central axis 110 of the tube 160. The curvature of the support surface 108 is defined by an equal length radius from a point 112 which is midway between the axis 110 of the tube and the inner cylindrical wall 102. In this illustration, the point 112 is located at the longitudinal axis of the surgical effector (surgical instrument) 28.

Figure 6B:
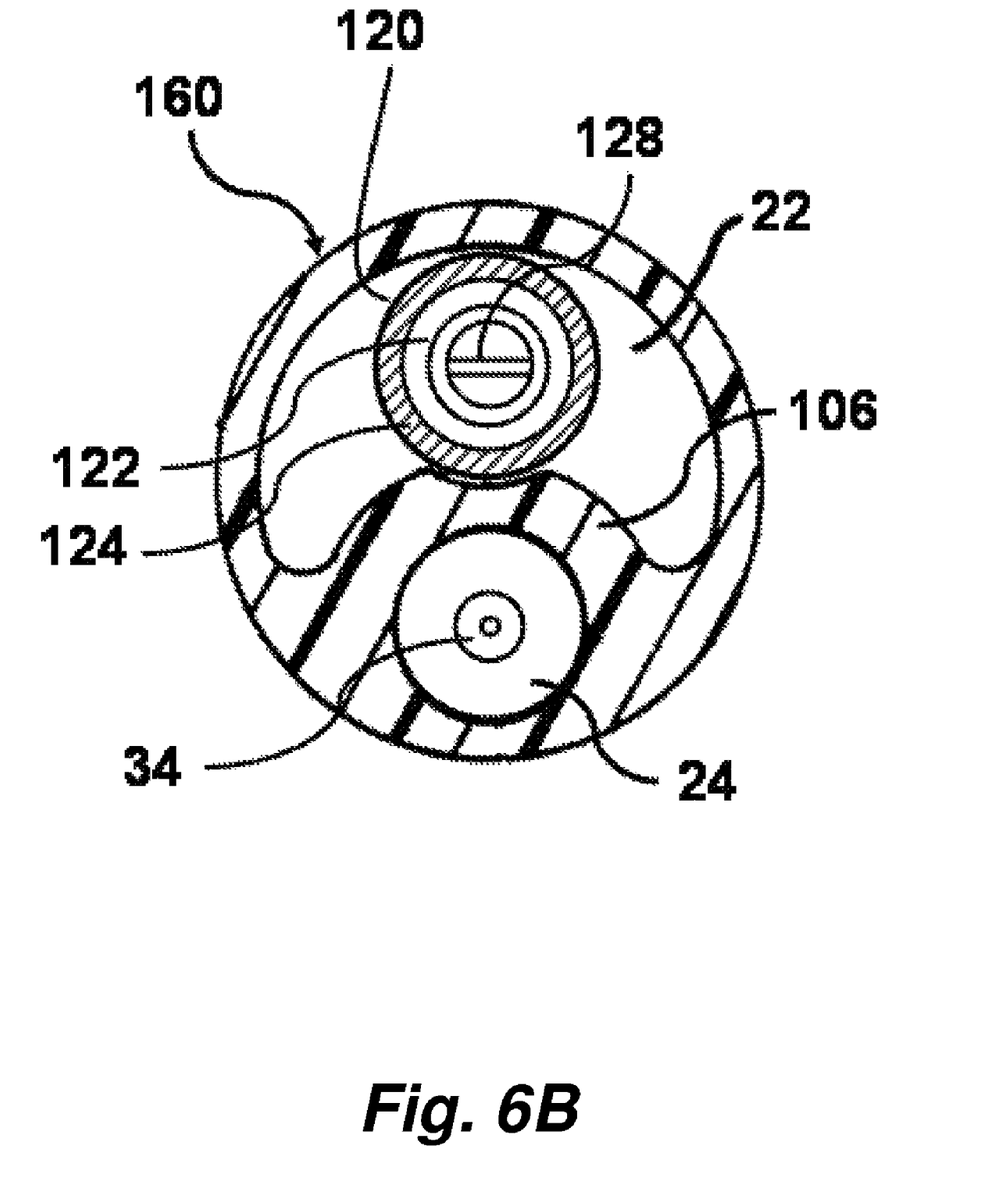

Having the shapes thus described, a longitudinal surgical effector having a dimension slightly less than the distance between the axis 110 and the wall 102 can fit within the instrument channel 22 and be supported by and retained in position when it rests on the support surface 108 and the interior surface 102, as is shown in FIG. 6B.

In this embodiment, the longitudinal axis of the instrument channel 22 becomes the same as the longitudinal axis of the surgical effector, and both axes are located at the point 112. Because the support surface 108 curves radially outward from the axis 110 of the tube 160 and toward the interior cylindrical wall 102, the surgical effector will be prevented from moving transversely within the instrument channel 22. The support surface 108 and the interior surface 102 are one example of means for supporting the auxiliary surgical instrument in the channel 22, however, other types and configurations of support means, either integral with the tube 160 or separate components, can be used as alternatives.

While the conduit is illustrated with a circular cross-section in FIG. 6A, the devices of this invention need not be so limited. Because the conduit conducts a gas the flow of which can be focused and/or shaped by the nozzle 34, the conduit can take essentially any convenient cross-sectional area. Moreover the shape of the conduit can vary along its length. By varying the shape of the conduit, different shaped channels 22 and/or effectors can be accommodated. Thus, the channel 22 and/or the effector also need not be limited to a circular cross-section, but can take any convenient shape.

In certain embodiments, the conduit and/or the channel, and/or the effector can be flexible thereby allowing the instrument to be conveniently shaped by the surgeon, e.g. to gain access to particular areas. In various embodiments, the handle can be flexible as well.

Figure 7:
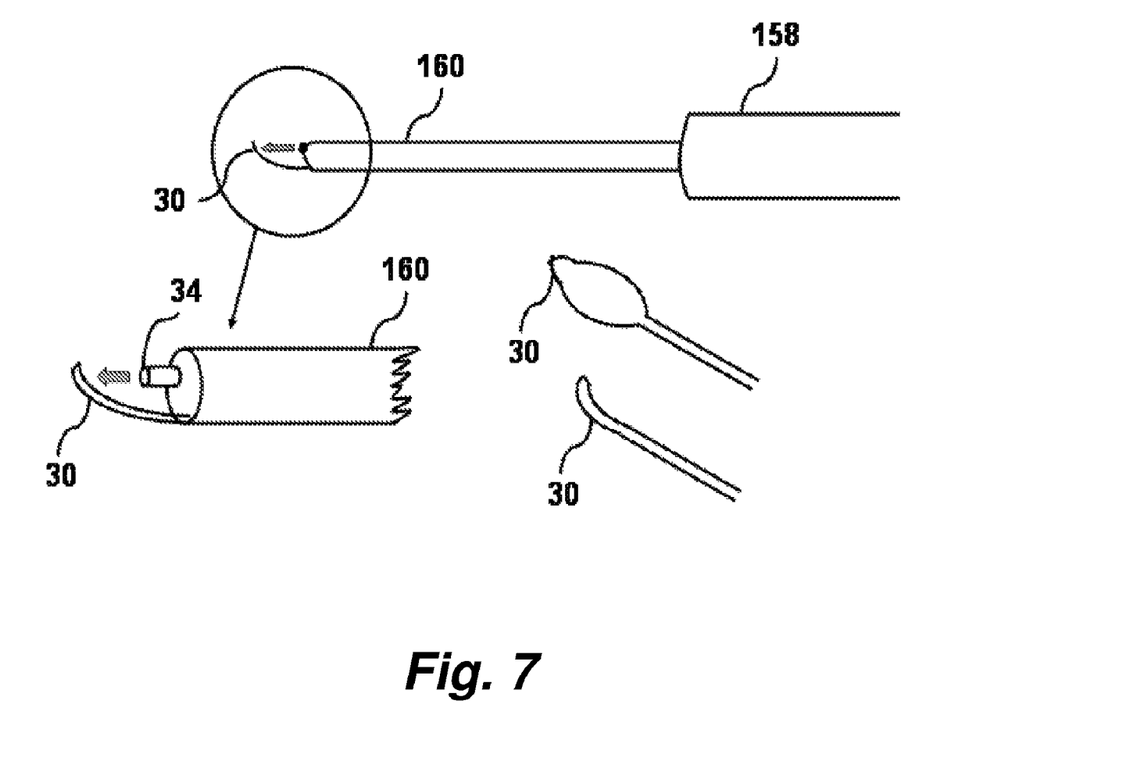

Although a variety of different types of auxiliary surgical instruments that have the necessary outer dimension and appropriate shape can be used with the probe 20, an exemplary standard electrosurgical coagulation and cutting electrode 120 is illustrated in FIG. 6B as the surgical effector 28. As illustrated in this figure, the electrosurgical electrode 120 is formed from a hollow metallic tube 122 upon which an exterior layer of insulating material 124 such as heat shrink tubing is connected. The tube 122 is preferably formed from stainless steel or aluminum, or other conducting, relatively non-reactive material. At the proximal end of the electrode 120, a metallic terminal end is mechanically and electrically connected to the tube 122. The terminal end 226 allows an electrical conductor connected to a conventional electrosurgical generator to be connected to the electrode 120 as the support equipment 152 (FIG. 5). At the distal end of the electrode 120 a metallic operating tip 128 is mechanically and electrically connected to the tube 122. The tip 128 may be of a variety of configurations adapted for the particular surgical procedure that the surgeon desires to accomplish. So long as the tip 128 extends no further transversely outward at any location than the exterior surface of the electrode 120, the electrode 120 can be inserted and removed from the channel 22 from the proximal end of the probe 20, while the probe is in place in the abdominal cavity 122 (FIG. 1). If the operating tip 128 is larger than the exterior surface of the electrode 120, the auxiliary surgical instrument is inserted in the instrument channel 22 before the probe is inserted in the cannula 124 (FIG. 1). Several operating tips are illustrated in FIG. 7.

As indicated above, the surgical probe 20 enhances visualization with a flow or jet of non-combustible gas (e.g. $CO_2$). The gas is delivered through conduit 24 and out nozzle or conduit port 34.

Figure 8:
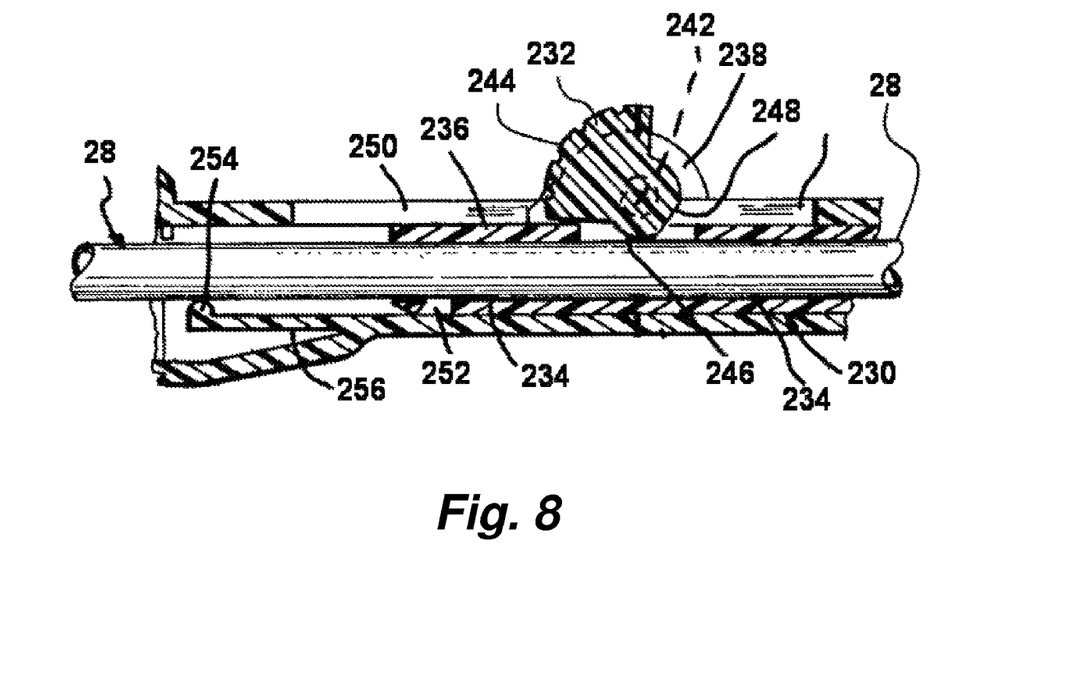
FIG. 8 illustrates an embodiment of probe 20 that allows extension and retraction of the surgical effector 26.

In certain embodiments, to allow the surgeon to control the extension and retraction of the surgical effector (instrument) 28, such as the electrode 120, without moving the probe within the cannula 124 (FIG. 5), the probe 20 can optionally include a slider member 230 which is illustrated in FIG. 8. The slider member 230 is movably retained within the interior 164 of the handle 158, to allow longitudinal movement along the instrument channel 22. The surgical effector 28 extends through a slot 234 in the slider member 230 and a lock roller member 232 applies frictional retaining force by which to selectively retain the slider member to the auxiliary surgical instrument 28. Once the slider member and the auxiliary surgical instrument are retained together, longitudinal movement of the slider member extends or retracts the distal end of the auxiliary surgical instrument from the end of the instrument channel at the distal end 18 of the probe 20.

The slot 234 of the slider member 230 in which the auxiliary surgical instrument is retained can have a U-shaped configuration that extends continuously longitudinally along and forms a part of the instrument channel 22. An inner cylindrical surface of the U-shaped slot 234 can be of uniform radius from the instrument axis. The straight leg portions of the U-shaped slot 234 integrally connect to a base portion 236 of the slider member 230. The base portion 236 extends the length of the slider member 230. A transversely center point on the bottom surface of the base portion 236 is located at approximately the same distance from the instrument axis 112 as the curved surface of the U-shaped slot 234, thus allowing the surgical effector to closely fit within the U-shaped slot 134.

At a middle longitudinal location along the length of the slider member 230, a pair of wing portions 238 extend upward from opposite transverse sides of the base portion 236. The wing portions 238 each have an opening formed therein for receiving a rotational axle 242 of the lock roller 232. The axle 242 of the lock roller 232 is snapped into the openings by slightly spreading the wing portions 238 and sliding the lock roller 232 between them until the axle 242 enters the openings. The resiliency of the wing portions returns them to the original position to hold the lock roller in position. As an alternative, the axle may not be made integral with the lock roller, but instead, a hole (not shown) can be formed through the lock roller at the location of the axle. A brass or other type of pin (also not shown) can be inserted through this hole and the openings to hold the lock roller in a pivotably connected condition to the wing portions. Use of the separate pin avoids the necessity to obtain sufficient resilience from the wing portions to allow them to accept the integral axle as shown.

The lock roller 232 includes an upper surface 244 that extends above the wing portions 238. The upper surface 244 has transverse slots or other types of ridges or indentions formed therein by which the surgeon can adequately frictionally engage the surface 244 and rotate the lock roller 232 about the axle 242.

A cam surface 246 is eccentrically positioned relative to the axle 242 at the lower end of the lock roller 232. By rotating the lock roller 232 in a clockwise direction as illustrated in FIG. 8, the cam surface 246 applies lateral force on the surgical effector 28 located within the U-shaped slot 234 of the slider member 230. Upon achieving a predetermined rotational position, a flat surface 248 of the cam surface 246 contacts the outer exterior of the surgical effector 28 and causes the lock roller 232 to be retained in position.

The amount of eccentric movement of the cam surface 246 and the flat surface 248 is sufficient to frictionally retain the auxiliary surgical instrument in the U-shaped slot 234 so that the instrument 28 moves in conjunction with the slider member 230. Thus, the extension and retraction of the operating tip of the auxiliary surgical instrument at the distal end of the probe is achieved by moving the slider member 230 forward and backward. As is shown in FIG. 8, an opening 250 is formed in the handle 158 to allow the lock roller 232 and wing portions 238 to move forward and rearwardly on the exterior of the handle 158.

The lock roller 232 is one of many alternative examples of a retaining means for selectively retaining the auxiliary surgical instrument to the slider member. Virtually any type of controllable retaining device capable of achieving a sufficient frictional engagement with the auxiliary surgical instrument to cause it to move with the slider member will suffice as an alternative to the lock roller 232.

Should the surgeon desire to fix the slider member 230 in a single location relative to the housing 158, the forward lower end of the U-shaped slot 234 has formed therein a notch 252 which is adapted to receive a ridge 254 of a resilient tang 256 located within the interior 168 of the handle 158. The resilient tang 256 deflects toward and away from the slider member and transversely with respect to the instrument channel 22, to allow the ridge 254 to snap within the notch 252 when the slider member 230 is moved to the forward position within the opening 250. With the ridge 254 engaged in the notch 252, the slider member 230 and the retained surgical effector 28 are held in a fixed position relative to the handle 158 of the probe 20. This feature allows the surgeon to fix the desired amount of extension of the surgical effector from the distal end 18 of the probe. By releasing the lock roller 232, adjusting the position of the surgical effector by grasping it from the rear end of the housing 158, and then rotating the lock roller 232 back into the retaining position, the position of the auxiliary surgical instrument in the probe 20 is changed. Alternatively, the surgeon can extend and retract the auxiliary surgical instrument by longitudinal movement of the slider member 230, provided that the slider member is not moved forward to the retained position.

In certain embodiments, it is preferred to arrange the cam surface 246 and the flat surface 248 to achieve retention between the slider member and the surgical effector 28 due to clockwise movement of the lock roller as shown in FIG. 8. Clockwise movement of the lock roller results from finger force which has a component tending to move the slider member rearward. Since a rearward component of finger force is required to overcome the force of the tang 256 to move the slider member rearward from the forwardmost position, the lock roller will not rotate to accidentally release the auxiliary surgical instrument when the slider member is moved rearward from the forward most position.

In certain embodiments, the probe provides the ability to achieve irrigation, aspiration or evacuation within the abdominal cavity from the distal end 18 of the probe. The irrigation, aspiration or evacuation can be achieved by fluid flow to or from the distal end 18 of the probe 20. In order to irrigate, aspirate and evacuate fluid (gas or liquid) from within the abdominal cavity and at the surgical site, the probe and/or surgical effector can, optionally, include an additional passageway to carry fluid or provide vacuum at the surgical site.

In certain embodiments, the probe 20 can additionally comprise a pressure relief valve connected in fluid communication with a port opening in the distal end of the probe. The pressure relief valve is operative to vent pressurized fluid upon the pressure of the fluid exceeding a predetermined level. The pressure relief valve is particularly useful in preventing over inflation of the abdominal cavity. The general nature of pressure relief valves is well known.

By providing a channel 22, in certain embodiments, extending from one end of the probe to the other it is apparent that the surgeon may exchange or substitute one surgical effector 28 for another by releasing the lock roller 232 and withdrawing the instrument during the procedure. Of course, for the slight amount of time during which one surgical effector is withdrawn and before another can be inserted in the probe, there will be a slight leak of gas through the channel 22. This slight leak of gas over a relatively short duration of time should not be sufficient to result in any significant reduction in the expansion of the abdominal wall, particularly since the inflation pump 128 (FIG. 1) should become operative immediately to add additional gas to the abdominal cavity to counteract the escaping gas. The longitudinal arrangement of the instrument channel in the manner described provides the substantial advantage of the surgeon not having to withdraw the probe from the cannula to exchange surgical effectors that have operating tips that do not exceed the outside dimensions of the instrument. Of course surgical effectors that do have larger operating tips can be inserted from the distal end of the probe prior to insertion in the cannula.

One of the substantial advantages offered by the probe 20 is the capability of instantly improving visibility at the surgical site simply by increasing gas flow through conduit 24 when necessary and/or desired. The availability of a gas jet to effect clearance of the surgical effector tip and surgical site of fluid and debris and to improve site visibility improves the accuracy, ease, reliability and efficacy of the surgical. A significant advantage offered by the probe 20 is the provision of the gas jet independent of any surgical effector activity. This permits the site to be cleared of fluids and/or debris and/or the surgical tip to be cleared prior to taking any action that might damage or alter the underlying tissues.

The probes 20 of this invention are useful in a wide variety of procedures. While the probe 20 is designed primarily for laparoscopic procedures, it will be appreciated that the probe can readily be applied to open surgical procedures as well. A primary advantage of the device of this invention includes the ability to clear the tissue of interest of fluid (e.g. blood) so that precise visualization and tissue division and coagulation are possible. Moreover, such visualization can be accomplished without performing any surgical activity.

A specific procedure where these considerations are particularly important is laparoscopic partial nephrectomy. During the operation, the parenchyma of the kidney must be transected in order to remove the cancer. The kidneys are extremely vascular organs, receiving 25 percent of the body's blood flow. To date there have been no efficient methods to cut the kidney tissue and coagulate the vessels with excellent visualization. It is crucial to directly view the areas to be cut so that an adequate margin of normal kidney around the tumor is removed.

Potential modifications or variations of the probe include, but are not limited to different shapes and sizes of the hand piece, variations in the positions of the controls of the surgical effector 38 and the gas 36, and various configurations of one, two, or more surgical effectors. Where the surgical effector is a cautery device, the configuration of the cautery blade itself can be modified.

In addition, while the probe 20 is illustrated with one or more removable surgical effectors, embodiments, where the surgical effector is an integral and fixed component of the probe 20 are also contemplated. Such "fixed" embodiments can be disposable or composed of materials suitable for repeated sterilization.

In certain embodiments, the probe 20, optionally comprises a relief valve 280 connected in fluid communication with the interior chamber or channel of the probe. The pressure relief valve 280 can be retained in a receptacle formed in the handle, and is operative to vent pressurized fluid or gas within the channel or interior chamber of the probe to the exterior of the handle upon the pressure of the fluid or gas exceeding a predetermined level. The pressure relief valve 280 is particularly useful in preventing over inflation of the abdominal cavity during use of the gas jet to clear a surgical site. The gas added to the abdominal cavity during can contribute to the pressure in the abdominal cavity. Although the back pressure sensor of the inflation pump may terminate the delivery of gas from the inflation pump to the abdominal cavity, the gas from the gas jet may continue to expand the abdominal wall. The limited venting from the incision around the may not be sufficient to prevent over-pressurization during use of the gas jet (e.g. at high pressure), but the pressure relief valve 280 will relieve this additional pressure once it exceeds the release point of the pressure relief valve 280. Since the interior chamber of the probe or the channel 22 communicates with the abdominal cavity 122 (FIG. 1) through the channel 22, the pressure relief valve 280 acts as an auxiliary or back up for the proper functionality of the back pressure sensor associated with the inflation pump. The incorporation of the pressure relief valve 280 in the probe 20 thus increases the measure of safety against the accidental over pressurization of the abdominal cavity during a minimally invasive surgery. The general nature of pressure relief valves is well known.

In certain embodiments, the gas jet can be used to deliver, e.g. pharmaceutical agents in addition to, or instead of, providing the site and/or probe clearance activity. In this context, the gas jet may be operated alone or in conjunction with the use of a surgical effector. The gas jet can be used to deliver any of a variety of agents. Virtually any agent can be so delivered. Preferred agents are pharmaceutically active agents capable of aerosolization and for which "direct" delivery to an internal tissue or other site is desired. Suitable agents include, but are not limited to disinfectants, vasoconstrictors, muscle relaxants, antibiotics, other pharmaceuticals, hemostatic agents, vaso-active agents, dyes, biological labeling agents (e.g. antibodies, spin labels, metal labels, fluorescent labels, and the like).

In certain embodiments, the gas jet can act as an effector itself. Thus, for example, by delivering a gas capable of freezing local vasculature and tissue cryosurgery can be performed, e.g. in lieu of cauterization.

In still another embodiment, this invention provides a kit comprising: a container containing a surgical probe as described herein. The kit can further comprise one or more surgical effectors that are insertable into the channel comprising the handle of the probe. Certain kits comprise an effector having surgical function selected from the group consisting of: visualizing tissue, anesthetizing tissue, incising tissue, cauterizing tissue, dissecting tissue, desiccating tissue, irrigating tissue, resecting tissue, delivering at least one therapeutic agent to tissue, aspirating fluids from tissue, biopsying tissue, and suturing tissue. In certain kits, one or more surgical effectors is a cauterization device. The kit can further comprising one or more replaceable tips for the cauterization device.

The kit can, optionally, further comprise instructional materials that direct use of the surgical device. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of performing a surgical procedure, said method comprising:
   providing a surgical probe comprising:
   a handle;
   at least one channel passing through said handle; and
   at least one conduit passing through said handle;
   wherein at least one effector element is inserted into or through said channel, which effector element effects one or more surgical functions; and
   wherein said conduit comprises a distal conduit port that directs gas out of said conduit to substantially remove debris and/or fluid from a surface disposed proximal to said effector element and/or from said effector element; and
   operating said probe to produce a flow of a non-combustible gas through said conduit wherein said gas comprises an aerosolized agent and said flow of gas delivers said agent to a surgical site.

2. The method of claim 1, wherein said agent is a pharmaceutically active agent.

3. The method of claim 2, wherein said pharmaceutically active agent is a microbicide and/or an antibiotic.

\* \* \* \* \*